US011311618B2

(12) United States Patent
Morel et al.

(10) Patent No.: US 11,311,618 B2
(45) Date of Patent: Apr. 26, 2022

(54) USE OF ADJUVANTS FOR THE PREVENTION AND/OR TREATMENT OF AUTOIMMUNE DISEASES

(71) Applicants: GLAXOSMITHKLINE BIOLOGICALS, SA, Rixensart (BE); SORBONNE UNIVERSITE, Paris (FR); INSTITUT NATIONAL DE LA SANTE ET DE LA RECHERCHE MEDICALE, Paris (FR)

(72) Inventors: Sandra Morel, Rixensart (BE); Charlotte Véronique Pouchy, Paris (FR); Benoit Laurent Salomon, Parai (FR); Nathalie Raoul Liliane Vanerheyde, Rixensart (BE)

(73) Assignees: INSTITUT NATIONAL DE LA SANTE ET DE LA RECHERCHE MEDICALE, Paris (FR); GLAXOSMITHKLINE BIOLOGICALS SA, Rixensart (BE); SORBONNE UNIVERSITE, Paris (FR)

( * ) Notice: Subject to any disclaimer, the term of this patent is extended or adjusted under 35 U.S.C. 154(b) by 284 days.

(21) Appl. No.: 16/061,524

(22) PCT Filed: Dec. 15, 2016

(86) PCT No.: PCT/EP2016/081181
§ 371 (c)(1),
(2) Date: Jun. 12, 2018

(87) PCT Pub. No.: WO2017/102939
PCT Pub. Date: Jun. 22, 2017

(65) Prior Publication Data
US 2020/0261569 A1 Aug. 20, 2020

(30) Foreign Application Priority Data
Dec. 17, 2015 (GB) .................................. 1522329

(51) Int. Cl.
| *A61K 39/39* | (2006.01) |
| *A61P 37/02* | (2006.01) |
| *A61K 9/107* | (2006.01) |
| *A61K 9/127* | (2006.01) |
| *A61K 39/00* | (2006.01) |

(52) U.S. Cl.
CPC .............. *A61K 39/39* (2013.01); *A61K 9/107* (2013.01); *A61K 9/127* (2013.01); *A61P 37/02* (2018.01); *A61K 2039/55555* (2013.01); *A61K 2039/55577* (2013.01)

(58) Field of Classification Search
None
See application file for complete search history.

(56) References Cited

U.S. PATENT DOCUMENTS

2007/0048261 A1* 3/2007 Mettens ................... A61P 25/00
424/85.2

FOREIGN PATENT DOCUMENTS

EP 2664332 B1 * 3/2017 ......... A61K 39/0005

OTHER PUBLICATIONS

Palmer et al. (Today's Dietitian, 13(11), p. 36, 2011). (Year: 2011).*
Epplen et al (Ann Neurol, 1997, 41, 341-352). (Year: 1997).*
Buenafe, A.C., et al, "Lipopolysaccharide pretreatment modulates the disease course in experimental autoimmune encephalomyelitis," Journal of Neuroimmunology, 2007, vol. 182, pp. 32-40.
Didierlaurent, A.M., et al, "Adjuvant system AS01: helping to overcome the challenges of modern vaccines," Expert Review of Vaccines, 2017, vol. 16, No. 1, pp. 55-63.
Eca Guimaraes, L., et al, "Vaccines, adjuvants and autoimmunity," Pharmacological Research, 2015, vol. 100, pp. 190-209.
Garcon, N., et al, "Understanding Modern Vaccines: Perspectives in Vaccinology," Elsevier, 2011, vol. 1, issue 1, pp. 89-113.
International Search Report for Appl. No. PCT/EP2016/081181 dated Feb. 28, 2017.
Qui. R., et al, "Regulatory T Cell Plasticity and Stability and Autoimmune Diseases," Clin Rev Allergy Immunol., Feb. 2020. vol. 58, No. 1, pp. 52-70.
Sadelain. M.W.J., et al, "Prevention of Type 1 Diabetes in NOD Mice by Adjuvant Immunotherapy," Diabetes, May 1990, vol. 39, pp. 583-589.
Van Der Laan, J.W., et al, "Safety of vaccine adjuvants: Focus on autoimmunity," Vaccine, 2015, vol. 33, pp. 1507-1514.
Written Opinion of the International Searching Authority for Appl. No. PCT/EP2016/081181 dated Feb. 28, 2017.

* cited by examiner

*Primary Examiner* — Celeste A Roney
(74) *Attorney, Agent, or Firm* — Birch, Stewart, Kolasch & Birch, LLP (57) ABSTRACT

The invention provides an adjuvant for use in the prevention and/or treatment of an autoimmune disease.

28 Claims, 9 Drawing Sheets

USE OF ADJUVANTS FOR THE PREVENTION AND/OR TREATMENT OF AUTOIMMUNE DISEASES

TECHNICAL FIELD

The present invention relates to adjuvants, in particular to the use of adjuvants in the prevention and/or treatment of autoimmune diseases.

BACKGROUND OF THE INVENTION

In many vaccines, antigens are in the form of purified or subunit proteins to improve their safety, but this comes at the expense of lower immunogenicity. Therefore, effective adaptive immune responses require the addition of adjuvants to trigger early inflammation and activate antigen presenting cells.

Aluminium adjuvant (alum) is widely used to promote antibody responses by inducing a Th2 response. Squalene-based adjuvants MF59 and adjuvant system (AS) 03 promote both Th1 and Th2 responses through their capacity to induce chemokine and cytokine release, leading to massive recruitment and activation of immune cells. As for the Toll-like-receptor ligand-based adjuvants AS04 and AS01, they induce Th1 and Th2 responses by directly activating innate immune cells.

Beyond the effects on effector responses, some studies revealed intriguing and paradoxical observations of the immunomodulatory impact of certain adjuvants in autoimmune diseases. Administration of complete Freund's adjuvant (CFA), used only in veterinary vaccines, induced protection and remission of type 1 diabetes in non-obese diabetic mice (Sadelain et al. (1990) Diabetes 39: 583). Also, administration of lipopolysaccharides (LPS), a natural TLR4 ligand used in research trials for veterinary vaccines, induced protection from experimental autoimmune encephalomyelitis (EAE), a mouse model of multiple sclerosis (Buenafe et al. (2007) J. Neuroimmunol. 182: 32). While these are interesting observations, both CFA and LPS are not suitable for human use because of toxicity.

Autoimmune diseases are caused by an immune response against constituents of the body's own tissues. More than 80 autoimmune diseases are known. Examples of autoimmune diseases include e.g. rheumatoid arthritis (RA), systemic lupus erythematosus (lupus), inflammatory bowel disease (IBD), multiple sclerosis (MS), type 1 diabetes mellitus, Guillain-Barré syndrome, Crohn's disease and psoriasis. Many of these diseases are chronic and can cause significant morbidity and disability. Treatment of autoimmune diseases is generally based on immunosuppression. While significant progress has been made in the treatment of autoimmune diseases, there is still a need for improved products and methods, which increase efficacy, reduce side-effects, are easy to administer, safe and can be used in long-term or even chronic treatment of these diseases.

SUMMARY OF THE INVENTION

It has now surprisingly been found that AS01 and AS03, two non-alum containing adjuvants suitable for, and approved for, human use, can induce almost complete prevention of autoimmune disease in an animal model, supporting their use in the prevention and/or treatment of autoimmune diseases in humans.

Accordingly, in a first aspect, the invention relates to an adjuvant for use in the prevention and/or treatment of an autoimmune disease, wherein the adjuvant does not comprise aluminium and is suitable for use in a human subject.

In a further aspect, there is provided a method for preventing and/or treating an autoimmune disease comprising administration of an adjuvant to a subject, wherein the adjuvant does not comprise aluminium and is suitable for use in a human subject.

In an even further aspect, the invention relates to the use of an adjuvant in the manufacture of a medicament for the prevention and/or treatment of an autoimmune disease, wherein the adjuvant does not comprise aluminium and is suitable for use in a human subject.

BRIEF DESCRIPTION OF THE FIGURES

FIG. 1: a, Representative picture of popliteal draining lymph nodes (dLN) 4 days after subcutaneous injection (footpads) of vaccine adjuvants. b, Typical flow cytometry analysis of Treg cells. c, Fold-increase of the percentage of Foxp3+ cells among CD4+ cells, compared to mice injected with PBS, in pLN 4 days and 7 days after subcutaneous injection of vaccine adjuvants. Cumulative data from 3 independent experiments. d, CD4+Foxp3−CD90.1+ cells were adoptively transferred prior to adjuvant injection and induction of Foxp3 on donor cells was evaluated at day 4 as a marker of pTreg cells. Represented is an example of analysis of Treg induction following AS01 treatment. e,f, Ex vivo suppressive activity of Treg cells purified from dLN of mice treated with AS01 4 days earlier. Representative data at a 1 to 2 Treg:Tconv cell ratio (e) and mean±SEM at different Treg:Tconv cell ratio from 4 independent experiments M. "Treg" cells is for regulatory T cells and "Tconv" cells is for conventional T cells.

FIG. 3: a, Clinical score of EAE (experimental autoimmune encephalomyelitis) in mice immunized to induce EAE at day 0 and treated with adjuvants at day −3 and 0. Cumulative data from 3 independent experiments. b, Representative proliferation (from 2 independent experiments) of 2D2 $MOG_{35-55}$-specific T cell 3 days after transfer in mice immunized to induce EAE (day 0) and treated with adjuvants (day −3). c, INF-γ and IL-17 production by MOG-reactive T cells from dLN of mice immunized 10 days earlier to induce EAE (day 0) and treated with AS01 or AS03 (day −3). d, Clinical score of EAE in mice immunized to induce EAE at day 0 and transferred the day before with Treg cells purified from PBS, AS01 or AS03 treated mice. e,f Percentage of Treg cells (e) and of integrin $αL^+$ and $αM^+$ among Treg and Tconv cells (f) in dLN at day 10 in mice immunized to induce EAE at day 0 and treated with AS03 at day −3. "Treg" cells is for regulatory T cells and "Tconv" cells is for conventional T cells.

DETAILED DESCRIPTION

As described above, in a first aspect, the invention relates to an adjuvant for use in the prevention and/or treatment of an autoimmune disease, wherein the adjuvant does not comprise aluminium and is suitable for use in a human subject.

Typically, the aim of the use of the invention, or of the method of the invention, is to prevent an autoimmune disease, including delaying onset of the disease, and/or treat such a disease, i.e. reduce the severity of such a disease, e.g. by reducing the cause of the autoimmune disease and/or reducing its symptoms. In one embodiment, a reduction of symptoms of more than 50%, such more than 75%, as determined according to the Examples herein, is achieved.
Adjuvants for Use in the Invention In some embodiments, the adjuvant comprises an immunologically active saponin, e.g. QS21. Adjuvants comprising saponins have been described in the art. Saponins are e.g. described in: Lacaille-Dubois and Wagner (1996) (A review of the biological and pharmacological activities of saponins. Phytomedicine Vol. 2: 363). Saponins are known as adjuvants in vaccines. For example, Quil A (derived from the bark of the South American tree Quillaja Saponaria Molina), was described by Dalsgaard et al. (1974) in "Saponin adjuvants" (Archiv. fur die gesamte Virusforschung, Vol. 44, Springer Verlag, Berlin, 243) to have adjuvant activity. Purified fractions of Quil A have been isolated by HPLC which retain adjuvant activity without the toxicity associated with Quil A (Kensil et al. (1991) J. Immunol. 146: 431). Quil A fractions are also described in U.S. Pat. No. 5,057,540 and "Saponins as vaccine adjuvants" (Kensil, C. R., Crit. Rev. Ther. Drug Carrier Syst., 1996, 12 (1-2): 1-55).

Two such fractions, suitable for use in the present invention, are QS7 and QS21 (also known as QA-7 and QA-21). QS21 is a preferred immunologically active saponin fraction for use in the present invention. QS21 has been reviewed in "Vaccine Adjuvants: preparation methods and research protocols" (Humana Press, Totowa, N.J., Edited by Derek T. O'Hagan, Chapter 15: "QS21 Adjuvant"). Particulate adjuvant systems comprising fractions of Quil A, such as QS21 and QS7, are e.g. described in WO 96/33739, WO 96/11711 and WO 07/068907.

In addition to the saponin component, the adjuvant preferably comprises a sterol. The presence of a sterol may further reduce reactogenicity of compositions comprising saponins, see e.g. EP0822831. Suitable sterols include beta-sitosterol, stigmasterol, ergosterol, ergocalciferol and cholesterol. Cholesterol is particularly suitable. Suitably, the immunologically active saponin fraction is QS21 and the ratio of QS21:sterol is from 1:100 to 1:1 w/w, such as from 1:10 to 1:1 w/w, e.g. from 1:5 to 1:1 w/w.

In some embodiments, the adjuvant used in the invention comprises a TLR (Toll-like receptor) agonist, such as a TLR4 agonist, e.g. 3D-MPL. The use of TLR agonists in adjuvants is well-known in art and has been reviewed e.g. by Lahiri et al. (2008, Vaccine 26: 6777). TLRs that can be stimulated to achieve an adjuvant effect include TLR2, TLR4, TLR5, TLR7, TLR8 and TLR9. TLR2, TLR4, TLR7 and TLR8 agonists, particularly TLR4 agonists, are preferred.

Suitable TLR4 agonists include lipopolysaccharides, such as monophosphoryl lipid A (MPL) and 3-O-deacylated monophosphoryl lipid A (3D-MPL). U.S. Pat. No. 4,436,727 discloses MPL and its manufacture. U.S. Pat. No. 4,912,094 and reexamination certificate B1 4,912,094 discloses 3D-MPL and a method for its manufacture. Another TLR4 agonist is glucopyranosyl lipid adjuvant (GLA), a synthetic lipid A-like molecule (see e.g. Fox et al. (2012) Clin. Vaccine Immunol. 19: 1633). In a further embodiment, the TLR4 agonist may be a synthetic TLR4 agonist, such as a synthetic disaccharide molecule, similar in structure to MPL and 3D-MPL, or may be synthetic monosaccharide molecules, such as the aminoalkyl glucosaminide phosphate (AGP) compounds disclosed in, for example, WO 98/50399, WO 01/34617, WO 02/12258, WO 03/065806, WO 04/062599, WO 06/016997, WO 06/12425, WO 03/066065, and WO01/90129. Such molecules have also been described in the scientific and patent literature as lipid A mimetics. Lipid A mimetics suitably share some functional and/or structural activity with lipid A, and in one aspect are recognised by TLR4 receptors. AGPs as described herein are sometimes referred to as lipid A mimetics in the art. In a preferred embodiment, the TLR4 agonist is 3D-MPL. TLR4 agonists, such as 3-O-deacylated monophosphoryl lipid A (3D-MPL), and their use as adjuvants in vaccines has e.g. been described in WO 96/33739 and WO 07/068907 and reviewed in Alving et al. (2012, Curr. Opin. in Immunol. 24: 310).

In a preferred embodiment of the invention, the adjuvant comprises both an immunologically active saponin and a TLR4 agonist, e.g. QS21 and 3D-MPL.

In a further preferred embodiment, the adjuvant comprises an immunologically active saponin and a TLR4 agonist, e.g. QS21 and 3D-MPL, in a liposomal formulation.

The term "liposome" when used herein refers to uni- or multilamellar lipid structures enclosing an aqueous interior. Liposomes and liposome formulations are well known in the art. Liposomal presentations are e.g. described in WO 96/33739 and WO 07/068907. Lipids which are capable of forming liposomes include all substances having fatty or fat-like properties.

Liposome size may vary from 30 nm to several μm depending on the phospholipid composition and the method used for their preparation. In particular embodiments of the invention, the liposome size will be in the range of 50 nm to 500 nm, and in further embodiments, in the range of 50 nm to 200 nm. Dynamic laser light scattering is a method used to measure the size of liposomes well known to those skilled in the art.

In a particularly suitable embodiment, liposomes used in the invention comprise DOPC and a sterol, in particular cholesterol. Thus, in a particular embodiment, adjuvants of the invention comprise QS21 in any amount described herein in the form of a liposome, wherein said liposome comprises DOPC and a sterol, in particular cholesterol.

In one embodiment, the adjuvant comprises between 5 and 100, such as between 10 and 75, e.g. 25 or 50 μg, of QS21 per dose and between 5 and 100, such as between 10 and 75, e.g. 25 or 50 μg of 3D-MPL per dose.

It is well known that for parenteral administration, solutions should be physiologically isotonic (i.e. have a pharmaceutically acceptable osmolality) to avoid cell distortion or lysis. An "isotonicity agent" is a compound that is physiologically tolerated and imparts a suitable tonicity to a formulation (e.g. immunogenic compositions of the invention) to prevent the net flow of water across cell membranes that are in contact with the formulation. Aqueous adjuvant compositions are known which contain 100 mM sodium chloride or more, for example adjuvant system A (AS) in WO 05/112991 and WO 08/142133 or the liposomal adjuvants disclosed in WO 07/068907.

In some embodiments, the isotonicity agent used for the composition is a salt. In other embodiments, however, the composition comprises a non-ionic isotonicity agent and the concentration of sodium chloride or the ionic strength in the composition is less than 100 mM, such as less than 80 mM, e.g. less than 30 mM, such as less 10 mM or less than 5 mM. In a preferred embodiment, the non-ionic isotonicity agent is a polyol, such as sorbitol. The concentration of sorbitol may be e.g. between about 3% and about 15% (w/v), such as between about 4% and about 10% (w/v). Adjuvants comprising an immunologically active saponin fraction and a TLR4 agonist wherein the isotonicity agent is salt or a polyol have been described in WO 10/142685, see e.g. Examples 1 and 2 in WO 10/142685.

In one embodiment, the adjuvant used in the invention is an oil-in-water emulsion. Suitably, said emulsion comprises a metabolisable oil in an amount of 0.5% to 20% of the total volume, The meaning of the term metabolisable oil is well known in the art. Metabolisable can be defined as 'being capable of being transformed by metabolism' (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. A particularly suitable metabolisable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly suitable oil for use in this invention. Squalene is a metabolisable oil by virtue of the fact that it is an intermediate in the biosynthesis of cholesterol (Merck index, 10th Edition, entry No. 8619).

Oil-in-water emulsions per se are well known in the art, and have been suggested to be useful as adjuvant compositions (EP 399843; WO 95/17210). Suitably, the metabolisable oil is present in an amount of 0.5% to 20% (final concentration) of the total volume of the immunogenic composition, suitably an amount of 1.0% to 10% of the total volume, suitably in an amount of 2.0% to 6.0% of the total volume.

In a specific embodiment, the metabolisable oil is present in a final amount of about 0.5%, 1%, 3.5% or 5% of the total volume of the immunogenic composition. In another specific embodiment, the metabolisable oil is present in a final amount of 0.5%, 1%, 3.57% or 5% of the total volume of the immunogenic composition. A suitable amount of squalene is about 10.7 mg per dose, suitably from 10.4 to 11.0 mg per dose.

Suitably the oil-in-water emulsion systems used in the present invention have a small oil droplet size in the sub-micron range. Suitably the droplet sizes will be in the range 120 to 750 nm, suitably sizes from 120 to 600 nm in diameter. Typically the oil-in water emulsion contains oil droplets of which at least 70% by intensity are less than 500 nm in diameter, in particular at least 80% by intensity are less than 300 nm in diameter, suitably at least 90% by intensity are in the range of 120 to 200 nm in diameter.

The oil-in-water emulsion according to the invention may comprise a sterol or a tocopherol, such as alpha-tocopherol. Sterols are well known in the art, for example cholesterol is well known and is, for example, disclosed in the Merck Index, 11th Edition, page 341, as a naturally occurring sterol found in animal fat. Other suitable sterols include β-sitosterol, stigmasterol, ergosterol and ergocalciferol. Suitably alpha-tocopherol or a derivative thereof, such as alpha-tocopherol succinate is present. Suitably alpha-tocopherol is present in an amount of between 0.2% and 5.0% (v/v) of the total volume of the immunogenic composition, suitably at an amount of 2.5% (v/v) in a 0.5 ml dose volume, or 0.5% (v/v) in 0.5 ml dose volume or 1.7-1.9% (v/v), suitably 1.8% in 0.7 ml dose volume. By way of clarification, concentrations given in v/v can be converted into concentration in w/v by applying the following conversion factor: a 5% (v/v) alpha-tocopherol concentration is equivalent to a 4.8% (w/v) alpha-tocopherol concentration. A suitable amount of alpha-tocopherol is about 11.9 mg per dose, suitably from 11.6 to 12.2 mg per dose.

The oil-in-water emulsion may comprise an emulsifying agent. The emulsifying agent may be present at an amount of 0.01 to 5.0% by weight of the immunogenic composition (w/w), suitably present at an amount of 0.1 to 2.0% by weight (w/w). Suitable concentration are 0.5 to 1.5% by weight (w/w) of the total composition. The emulsifying agent may suitably be polyoxyethylene sorbitan monooleate (polysorbate 80 or Tween 80). In a specific embodiment, a 0.5 ml dose volume contains 1% (w/w) Tween 80, and a 0.7 ml dose volume contains 0.7% (w/w) Tween 80. In another specific embodiment the concentration of Tween 80 is 0.2% (w/w). A suitable amount of polysorbate 80 is about 4.9 mg per dose, suitably from 4.6 to 5.2 mg per dose.

Span 85 (polyoxyethylene sorbitan trioleate) may also be present, for example at a level of 1%. An example of oil-in-water emulsion adjuvant comprises Span85 for use in the invention is given and detailed in EP0399843B, also known as MF59.

In a preferred embodiment, the adjuvant is an oil-in-water emulsion comprising squalene, alpha-tocopherol and a surfactant, i.e. the emulsion comprises squalene, alpha-tocopherol and a surfactant, e.g. polysorbate 80, in an aqueous phase. Preparation of such adjuvants is e.g. described in WO 95/17210 and WO 06/100109. In one embodiment, the emulsion comprises 2-10% (v/v) squalene, from 2-10% (v/v) alpha-tocopherol and from 0.3-3% (v/v) Tween 80. Preferably, the emulsion comprises 2.5% squalene (v/v), 2.5% alpha-tocopherol (v/v), 0.9% polyoxyethylene sorbitan monooleate (v/v) (Tween 80).

Autoimmune Diseases to be Prevented and/or Treated

As explained above, the invention relates to the use of adjuvants for the prevention and/or treatment of autoimmune diseases. The following diseases have been classified as autoimmune diseases: Acute disseminated encephalomyelitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune hepatitis, Autoimmune inner ear disease (AIED), Axonal & neuronal neuropathy (AMAN), Behcet's disease, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid/benign mucosal pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, IgA Nephropathy, IgG4-related sclerosing disease, Inclusion body myositis (IBM), Interstitial cystitis (IC), Juvenile arthritis, Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis (MS), Myasthenia gravis, Myositis, Narcolepsy, Neuromyelitis optica, Neutropenia, Ocular cicatricial pemphigoid, Optic neuritis, Palindromic rheumatism (PR), PANDAS (Pediatric Autoimmune Neuropsychiatric Disorders Associated with *Streptococcus*), Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome (polyneuropathy, organomegaly, endocrinopathy, monoclonal gammopathy, skin changes), Polyarteritis nodosa, Polymyalgia rheumatic, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Reiter's syndrome, Relapsing polychondritis, Restless legs syndrome (RLS), Retroperitoneal fibrosis, Rheumatic fever, Rheumatoid arthritis (RA), Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Wegener's granulomatosis (now termed Granulomatosis with Polyangiitis (GPA).

Preferred Disease to be Prevented and/or Treated According to the Invention Include:

Rheumatoid Arthritis

In people with rheumatoid arthritis, the immune system predominantly targets the lining (synovium) that covers various joints. Inflammation of the synovium is usually symmetrical (occurring equally on both sides of the body) and causes pain, swelling, and stiffness of the joints. These features distinguish rheumatoid arthritis from osteoarthritis, which is a more common and degenerative "wear-and-tear" arthritis. Currently available therapy focuses on reducing inflammation of the joints with anti-inflammatory or immunosuppresssive medications. Sometimes, the immune system may also target the lung, blood vessels, or eye; occasionally patients may also develop symptoms of other autoimmune diseases such as Sjogren's the inflammation, itching, and scaling.

Multiple Sclerosis

Multiple sclerosis is a disease in which the immune system targets nerve tissues of the central nervous system. Most commonly, damage to the central nervous system occurs intermittently, allowing a person to lead a fairly normal life. At the other extreme, the symptoms may become constant, resulting in a progressive disease with possible blindness, paralysis, and premature death. Some medications such as beta interferon are helpful to people with the intermittent form of multiple sclerosis. In young adults, multiple sclerosis is the most common disabling disease of the nervous system.

Immune-Mediated or Type 1 Diabetes Mellitus

Type 1 diabetes mellitus results from autoimmune destruction of the insulin-producing cells of the pancreas. Insulin is required by the body to keep the blood sugar (glucose) level under control. High levels of glucose are responsible for the symptoms and the complications of the disease. However, most of the insulin-producing cells are destroyed before the patient develops symptoms of diabetes. Symptoms include fatigue, frequent urination, increased thirst, and possible sudden confusion. Type 1 diabetes mellitus is usually diagnosed before the age of 30 and may be diagnosed as early as the first month of life. Together with Type 2 diabetes (not considered an autoimmune disease), diabetes mellitus is the leading cause of kidney damage, loss of eyesight, and leg amputation. Close control of sugar levels decreases the rate at which these events occur.

Inflammatory Bowel Diseases

This medical term is used for both Crohn's disease and ulcerative colitis, two diseases in which the immune system attacks the gut (intestine). Patients may have diarrhea, nausea, vomiting, abdominal cramps, and pain that can be difficult to control. Illness in afflicted individuals can result from intestinal inflammation and from side effects of the drugs used for the disease. For example, daily use of high-dose corticosteroid (prednisone) therapy, which is needed to control severe symptoms of Crohn's disease, can predispose patients to infections, bone thinning (osteoporosis), and fractures.

Systemic Lupus Erythematosus

Patients with systemic lupus erythematosus most commonly experience profound fatigue, rashes, and joint pains. In severe cases, the immune system may attack and damage several organs such as the kidney, brain, or lung. For many individuals, symptoms and damage from the disease can be controlled with available anti-inflammatory medications.

Psoriasis

Psoriasis is an immune system disorder that affects the skin, and occasionally the eyes, nails, and joints. Psoriasis may affect very small areas of skin or cover the entire body with a buildup of red scales called plaques. The plaques are of different sizes, shapes, and severity and may be painful as well as unattractive. Bacterial infections and pressure or trauma to the skin can aggravate psoriasis. Most treatments focus on topical skin care to relieve the inflammation, itching, and scaling.

Scleroderma

This autoimmune disease results in thickening of the skin and blood vessels. Almost every patient with scleroderma has Raynaud's, which is a spasm of the blood vessels of the fingers and toes. Symptoms of Raynaud's include increased sensitivity of the fingers and toes to the cold, changes in skin color, pain, and occasionally ulcers of the fingertips or toes. In people with scleroderma, thickening of skin and blood vessels can result in loss of movement and shortness of breath or, more rarely, in kidney, heart, or lung failure.

Autoimmune Thyroid Diseases

Hashimoto's thyroiditis and Grave's disease result from immune system destruction or stimulation of thyroid tissue. Symptoms of low (hypo-) or overactive (hyper-) thyroid function are nonspecific and can develop slowly or suddenly; these include fatigue, nervousness, cold or heat intolerance, weakness, changes in hair texture or amount, and weight gain or loss. The diagnosis of thyroid disease is readily made with appropriate laboratory tests. The symptoms of hypothyroidism are controlled with replacement thyroid hormone pills; however, complications from over- or under-replacement of the hormone can occur. Treatment of hyperthyroidism requires long-term anti-thyroid drug therapy or destruction of the thyroid gland with radioactive iodine or surgery. Both of these treatment approaches carry certain risks and long-term side effects.

In a preferred embodiment, the autoimmune disease to be prevented and/or treated is a disease affecting the nervous system, such as the central nervous system. In an even more preferred embodiment, the autoimmune disease is multiple sclerosis. In a further more preferred embodiment, the autoimmune disease it type 1 diabetes. In a further preferred embodiment, the autoimmune disease is acute disseminated encephalomyelitis.

In particular, adjuvants comprising an oil-in-water emulsion, e.g. comprising squalene, alpha-tocopherol and polysorbate 80 in an aqueous phase, are preferred for the prevention and/or treatment of diseases affecting the nervous system, such as the central nervous system, e.g. multiple sclerosis.

Treatment Options

In preferred embodiments, the method of the invention, or use of the invention, comprises multiple administrations of the adjuvant, for example, at least 2, at least 3, at least 4, at least 5, or at least 10 administrations of the adjuvant. In one embodiment, the time interval between each of the administrations is between 1 day and 6 months, e.g. the interval may be from 1 week to 1 month between each administration.

In a preferred embodiment, the subject is a human subject. The human subject to be treated using the method of the invention may be of any age. In one embodiment, however, the human subject is more than 18 years of age when the treatment is initiated. In further embodiments, the subject is more than 40 years of age, such as more than 50 years of age, e.g. more than 60 years of age. The subject may be male or female.

In one embodiment, the adjuvant is for use in the prevention of an autoimmune disease in a human subject who is pre-disposed to develop an autoimmune disease, for example, a subject who is pre-disposed to develop multiple sclerosis or a subject who is pre-disposed to develop type 1 diabetes. A human subject who is pre-disposed to develop an autoimmune disease can, for example, be a subject who shows early clinical signs of an autoimmune disease, a subject who has a genetic risk of developing an autoimmune disease or a subject who has specific auto-antibodies.

A person pre-disposed to develop multiple sclerosis is e.g. a person having CIS (clinically isolated syndrome) —a first and single neurologic episode of inflammation or demyelination in the central nervous system lasting at least 24 hours, in particular when lesions consistent with multiple sclerosis are seen on MRI.

A person pre-disposed to develop type 1 diabetes is e.g. a person having auto-antibodies, such as autoantibodies GADA, IA-2A and/or mIAA (Sosenko et al. (2013) Diabetes Care 36: 2615).

The adjuvant may be administered via various suitable routes, including parenteral, such as intramuscular, intradermal or subcutaneous administration. Suitably, the adjuvant compositions used in the present invention have a human dose volume of between 0.05 ml and 1 ml, such as between 0.1 and 0.5 ml, in particular a dose volume of about 0.5 ml, or 0.7 ml.

The adjuvant may be given as monotherapy or in combination with other substances, e.g. other substances known to have a therapeutic or prophylactic effect on autoimmune diseases.

The teachings of all references in the present application, including patent applications and granted patents, are herein fully incorporated by reference. The terms 'comprising', 'comprise' and 'comprises' herein are optionally substitutable with the terms 'consisting of', 'consist of', and 'consists of', respectively. The invention will be further described by reference to the following, non-limiting, examples:

EXAMPLES

Example 1—Methods

Mice

WT mice were purchased from Janvier Labs (France). 2D2 T-cell receptor transgenic mice, specific for myelin oligodendrocyte glycoprotein, were purchased from the Jackson Laboratory. Foxp3-IRES-GFP knock-in (Foxp3GFP) mice were kindly provided by Pr. Bernard Malissen. 2D2 and Foxp3GFP mice were backcrossed with CD90.1 congenic animals. All mice were on a C57Bl/6 background. Mice were housed under specific pathogen-free conditions and were studied at 7-14 week of age. All experimental protocols were approved by the local ethics committee and are in compliance with European Union guidelines.

Reagents

AS01 is composed of MPL (1 mg/ml), QS-21 (1 mg/ml) and liposomes. AS03 is composed of alpha-tocopherol (23.72 mg/ml), squalene oil (21.38 mg/ml) and polysorbate 80 (9.72 mg/ml). AS04 is composed of MPL (0.1 mg/ml) and alum (1 mg/ml). Freund's adjuvants were purchased from Sigma-Aldrich. Incomplete form (IFA) contains 85% of paraffin oil and 15% of mannide monooleate. Complete form (CFA) adds *Mycobacterium tuberculosis* (H37Ra) heat killed and dried at a concentration of 1 mg/ml.

Administration of Adjuvants

Mice received 30 µl of vaccine adjuvant or PBS by subcutaneous route in left hind footpads. To analyze their effect, left popliteal draining lymph nodes (dLN) and non-draining right brachial lymph nodes were collected at different time points. In mice that were immunized to induce EAE (experimental auto-immune encephalomyelitis), they received 100 µl of vaccine adjuvant or PBS by subcutaneous route at the base of the tail and at the upper back 3 days before and on the day of EAE (experimental autoimmune encephalomyelitis) induction.

Flow Cytometry Analyses

Cells from lymph nodes were mechanically dissociated and resuspended in PBS 3% SVF. They were first treated with 2.4G2 antibody to block the Fc receptor and stained with the following antibodies: anti-CD45 (30-F11), anti-CD3 (145-2C11), anti-CD4 (RM4-5), anti-CD8 (53-6.7), anti-CD25 (PC61), anti-Foxp3 (MF23), anti-CTLA-4 (UC10-4F10-11), anti-GITR (DTA-1), anti-ICOS (17G9), anti-Ki-67 (B56). All antibodies were obtained from BD Biosciences. Intracellular staining was performed using the Intracellular Fixation & Permeabilization Buffer Set from eBioscience. Cells were acquired on a BD LSRII cytometer and analyzed using FlowJo software.

Treg Peripheral Induction Assessment

Lymph nodes (brachial, axillary, cervical, and inguinal) and spleen cells of Foxp3$^{GFP}$ CD90.1 mice were isolated, treated as above and stained with an anti-CD4 antibody. CD4$^+$GFP$^-$ cells (Tconv) were purified using a BD FACSAria II then intravenously injected in WT mice ($10^6$ cells/mouse). The following day, mice received 30 µl of vaccine adjuvant or PBS by subcutaneous route in left hind footpads. Three days after, dLN were collected and cells were stained with anti-CD4, anti-CD90.1 (OX-7), anti-CD90.2 (30-H12) and anti-Foxp3 antibodies. Foxp3 induction in CD90.1 transferred cells was evaluated by flow cytometry.

In Vitro Treg Suppression Assay

Foxp3$^{GFP}$ mice received 100 µl of vaccine adjuvant or PBS by subcutaneous route at the base of the tail and at the upper back. Brachial and inguinal lymph nodes were collected at 3 or 7 days. Cells were isolated and stained as described above. CD4$^+$GFP$^-$ cells (Tconv) and CD4$^+$GFP$^+$ cells (Treg) were then sorted using BD FACSAria II. Tconv cells were labeled with CellTrace Violet Proliferation Kit (Life technologies) and plated in 96-well plate at $2.5 \times 10^4$ cells/well with splenocytes from CD3$^{-/-}$ mice at $7.5 \times 10^4$ cells/well. Culture medium was supplemented with anti-CD3 (KT3) from BioXCell at 0.05 µg/ml. Treg cells were then added at different ratios from 1:1 to 1:16. At day 3, CellTrace dilution was assessed by flow cytometry.

EAE Induction

Mice were immunized by subcutaneous injection of 100 µg of MOG$_{35-55}$ peptide (PolyPeptide) emulsified in 100 µl of CFA (Sigma-Aldrich) supplemented with 50 µg of heat-killed *Mycobacterium tuberculosis* H37Ra (BD Biosciences). Animals were additionally injected intravenously with 200 ng of *Bordetella pertussis* toxin (Enzo) at the time of, and two days following immunization. The clinical evaluation was performed on a daily basis by a 5-point scale ranging from 0, no clinical sign; 1, limp tail; 2, limp tail, impaired righting reflex, and paresis of one limb; 3, hindlimb paralysis; 4, hindlimb and forelimb paralysis; 5, moribund.

Cytokine Measurement

Ten days after EAE induction, brachial and inguinal dLN were collected. Cells were cultured with 1 µg/ml of MOG$_{35-55}$ peptide in 96-well plate at $2 \times 10^5$ cells/well. At day 3, supernatants were harvested to measure INF-γ and IL-17 secretions by ELISA (eBioscience).

T Cell Priming Evaluation

Lymph nodes and spleen cells from 2D2 CD90.1 mice were stained with the following biotin-labeled antibodies: anti-CD19 (6D5), anti-CD11b (M1/70), anti-CD11c (N418), anti-CD8 (53-6.7) and anti-CD25 (7D4) and then were coated with anti-biotin microbeads (Miltenyi Biotec). After magnetic sorting, cells of the CD4$^+$ enriched negative fraction were labeled with CellTrace Violet Proliferation Kit and were intravenously injected in naive mice ($10^6$ cells/mouse). The following day, mice were immunized with MOG$_{35-55}$ peptide as for EAE induction. CellTrace dilution of CD4$^+$CD90.1$^+$Vβ11$^+$ (T-cell receptor transgene) cells was assessed by flow cytometry from brachial and inguinal lymph nodes at day 3. In mice receiving adjuvants, they were injected with 100 µl of vaccine adjuvant or PBS by subcutaneous route at the base of the tail and at the upper back.

Treg Cell Adoptive Transfer

Foxp3$^{GFP}$ CD90.1 mice received 100 µl of vaccine adjuvant or PBS by subcutaneous route at the base of the tail and at the upper back. At day 3, brachial and inguinal lymph nodes were collected and cells were stained with anti-CD4 antibody. CD4$^+$GFP$^+$ cells (Treg) were then purified using BD FACSAria II and intravenously injected in WT mice ($1 \times 10^6$ cells/mouse). The following day, mice were immunized with MOG$_{35-55}$ peptide as previously described in EAE induction.

Statistical Analysis

Statistical analyses were performed using GraphPad Prism Software. Statistical significance was determined using the two-tailed nonparametric Mann-Whitney U test. *$p<0.05$, $p<0.01$, *$p<0.001$. Means±SEM were used throughout the figures.

Figure 1:
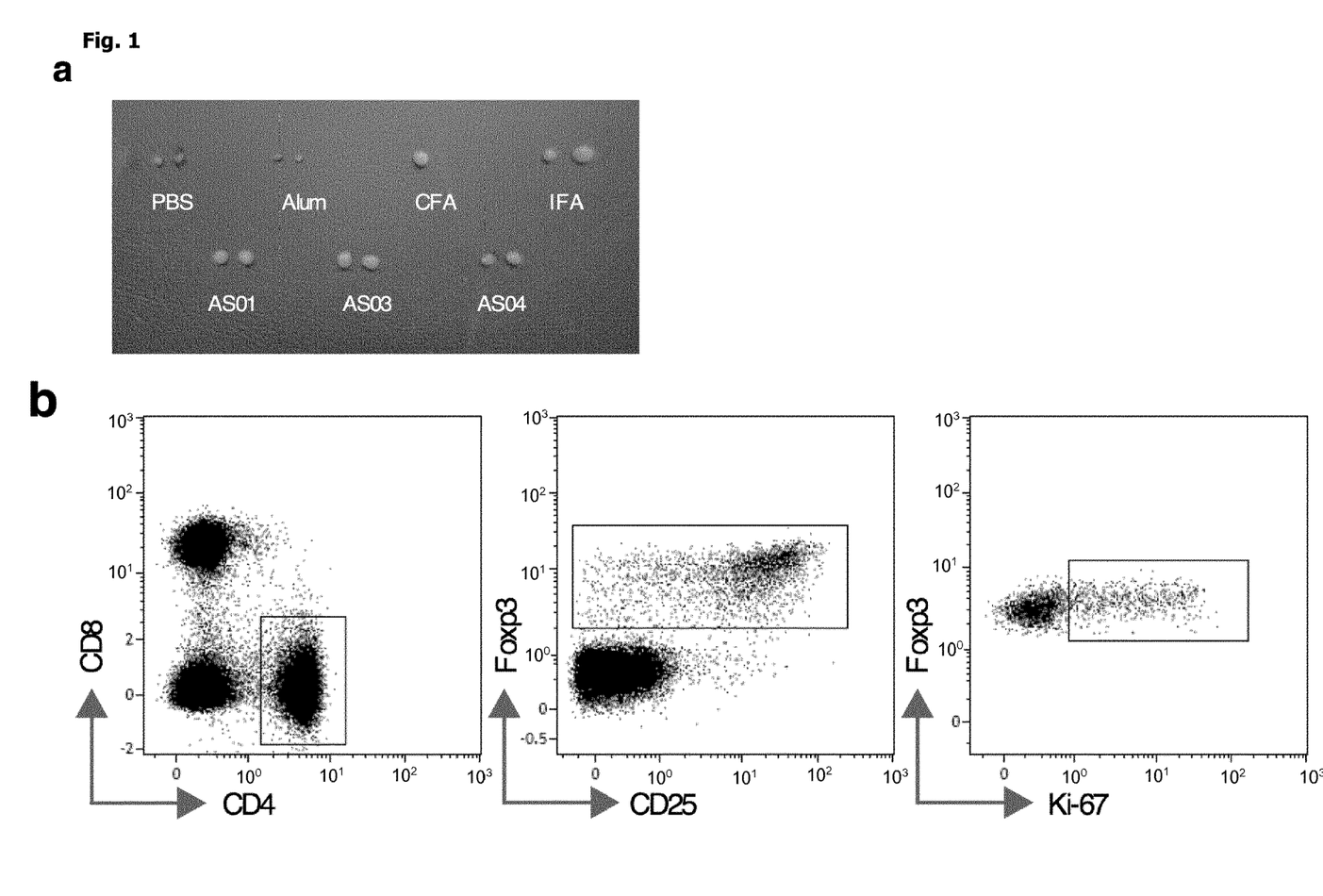
Figure 2:
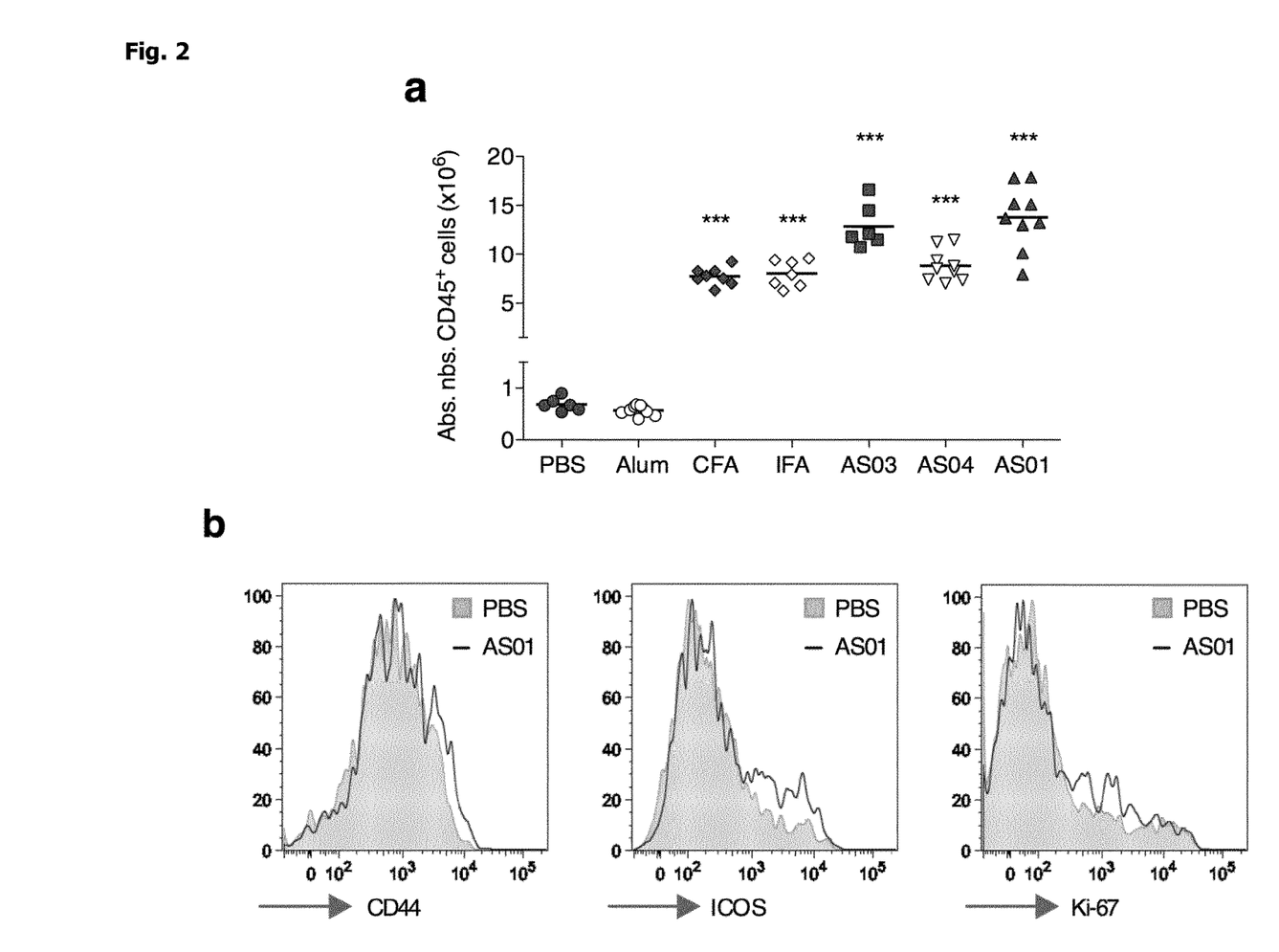
FIG. 2: a, Absolute number of $CD45^+$ cells in dLN 4 days after subcutaneous injection of vaccine adjuvants. Cumulative data from 3 independent experiments. b, Representative expression of CD44, ICOS and KI-67 in Treg cells from dLN 4 days after subcutaneous injection of AS01. c, In vitro suppressive activity of Treg cells purified from dLN 3 days after subcutaneous injection of vaccine adjuvants. d, Representative Foxp3 expression in Treg cells from dLN 3 days after subcutaneous injection of AS01. e, In vitro suppressive activity of Treg cells purified from dLN 7 days after subcutaneous injection of AS01. "Treg" cells is for regulatory T cells.

Example 2—Vaccine Adjuvants Induce Transient Preferential Expansion of Treg Cells CFA, incomplete Freund's adjuvants (IFA), AS01, AS03 and AS04 were administered subcutaneously to mice. After 4 days, a massive inflammation and swelling of the draining lymph nodes (dLN) was observed (FIG. 1a). The cellularity of these dLN was increased by 11 to 20 fold (FIG. 2a). By contrast, injection of alum had no effect on size and cell numbers of dLN.

Treg cells were then analyzed by flow cytometry (FIG. 1b). Except for alum, we observed a rapid increase (day 4) of Treg cell proportions among CD4$^+$ cells after injection of the different adjuvants, up to 1.9 fold compared to the PBS-injected mice (FIG. 1c). This Treg cell expansion was associated with an activated phenotype, as shown by an increased expression of CD44, ICOS and Ki-67 (FIG. 2b). These Treg cell expansion and activation were transient since it was no longer present at day 7, except for IFA (FIG. 1c). Treg cell expansion driven by adjuvant injections was due to thymic Tregs (tTregs) accumulation and not to increased induction of peripheral Treg. Indeed, Foxp3 expression was not induced by adjuvants in adoptively transferred CD4+Foxp3− cells (FIG. 1d). These data revealed the in vivo activation of tTreg cells by new generation adjuvants.

We then assessed the effect of vaccine adjuvant administration on Treg cell activity by classical in vitro suppression assay. Alum, Freund's adjuvant, AS03 and AS04 had no effect on Treg cell function (FIG. 2c), while AS01 partially reduced their suppressive activity and Foxp3 expression (FIGS. 1e and 1f and 2d). This effect was observed at day 4 but not anymore at day 7 (FIG. 2e). Thus, administration of new generation adjuvants did not impair, or only marginally, the suppressive function of Treg cells.

Example 3—EAE Prevention by Administration of AS01 and AS03 Adjuvants

Figure 3:
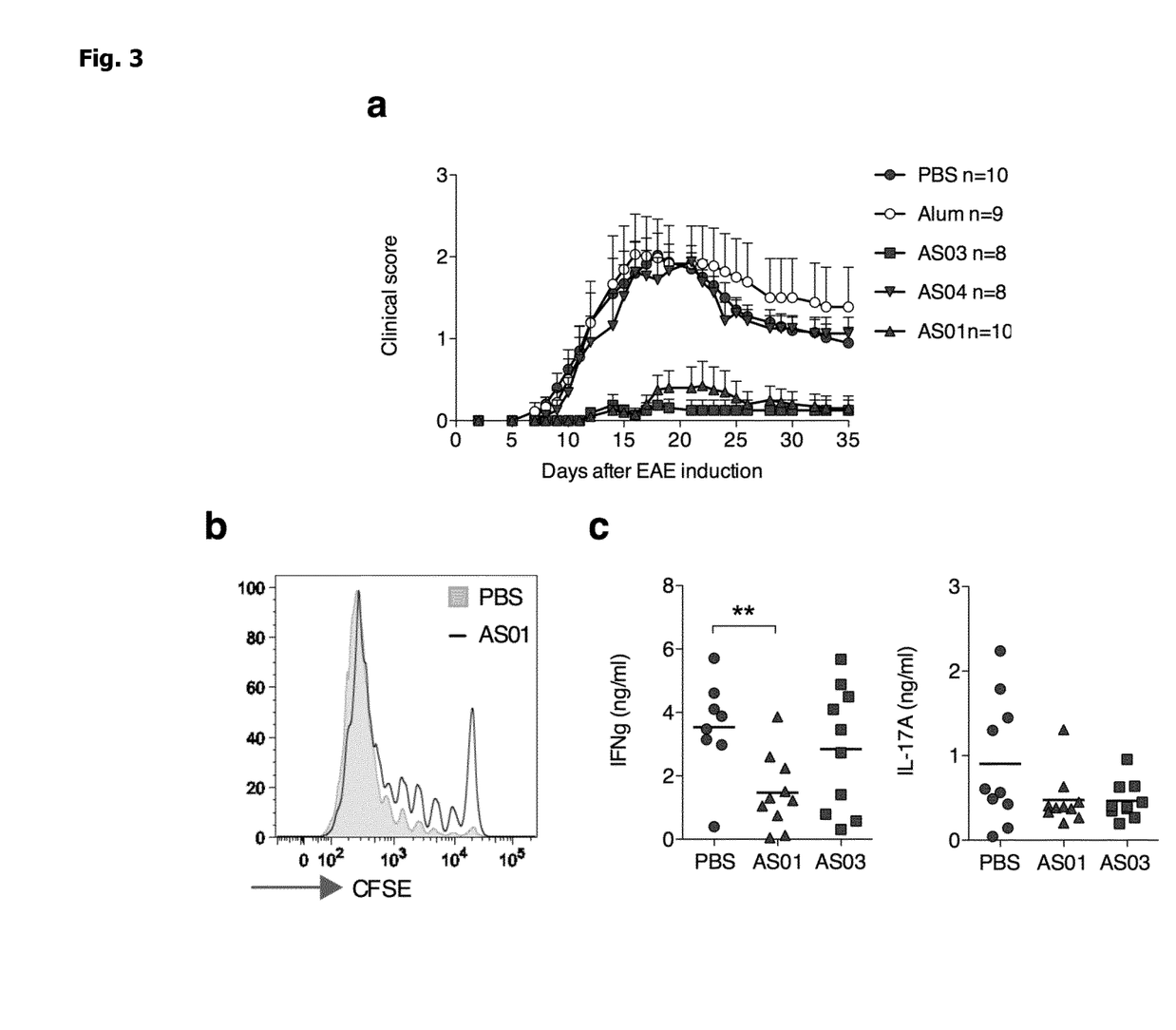
Figure 4:
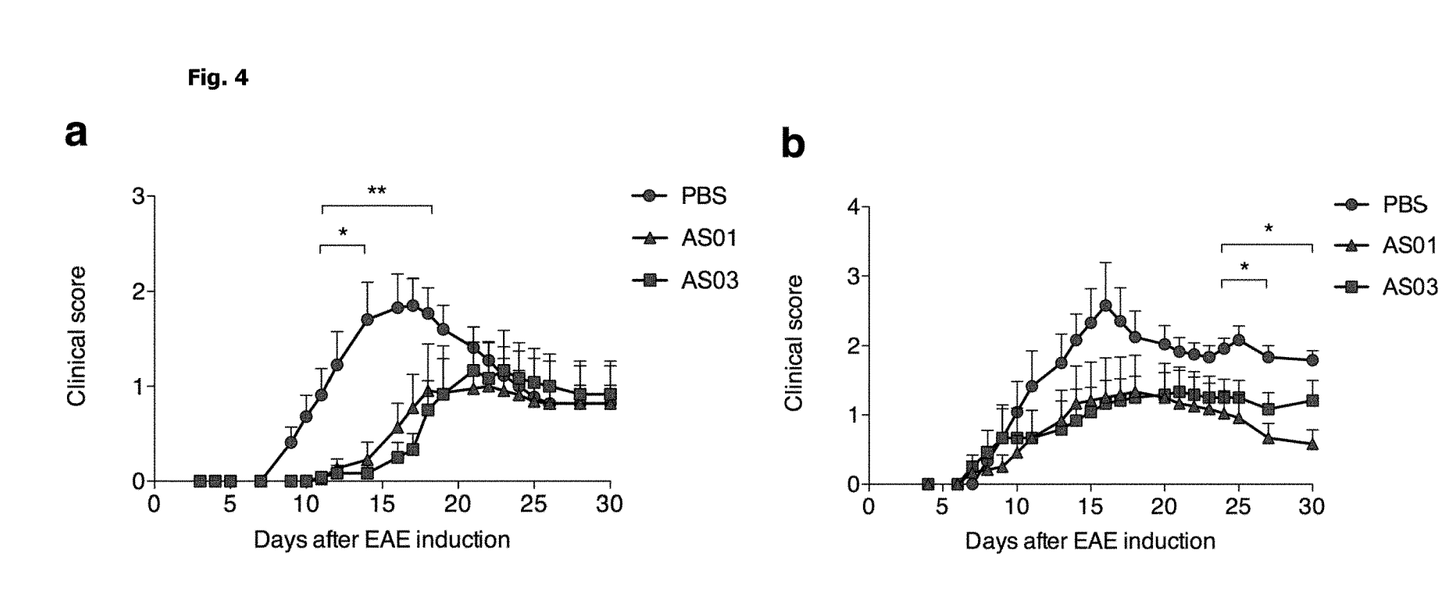
FIG. 4: a, b Clinical score of EAE (experimental autoimmune encephalomyelitis) in mice immunized to induce EAE at day 0 and treated with AS01 or AS03 at day −3 (a) or day 0 (b). Cumulative data from 3 independent experiments. c,d Proportions of CCR6+ cells and CXCR3+ cells (c) and of integrin α4+ cells and integrin αL+ cells (d) among Treg cells and Tconv cells in dLN at day 10 in mice immunized to induce EAE at day 0 and treated with AS03 at day 0 and −3. "Treg" cells is for regulatory T cells and "Tconv" cells is for conventional T cells.

In order to evaluate the effects of vaccine adjuvants on tolerance induction in a physiopathological context, we tested adjuvant treatments in the EAE autoimmune model. Strikingly, 2 injections of AS01 or AS03, 3 days before and at the time of immunization, induced almost complete prevention from disease development. Mean clinical scores were below 0.14-0.17, compared to 1.17 in controls. In contrast, AS04 and alum had no effect on EAE (FIG. 3a). After only one injection of AS01 or AS03 performed 3 days before, or at the time of immunization, EAE was significantly delayed or reduced, respectively (FIGS. 4a and 4b). Thus, AS01 and AS03 have strong preventing effect on EAE.

We next investigated priming and cytokine polarization of auto-reactive Tconv cells. T-cell proliferation was assessed after adoptive transfer of 2D2 transgenic mice expressing a transgenic I-$A^b$-restricted T cell receptor specific for $MOG_{35-55}$ peptide (Bettelli et al. (2003) J. Exp. Med. 197: 1073) prior to EAE induction. AS01 administration slightly reduced the proliferation of $MOG_{35-55}$-specific T cells at day 3 in dLN, whereas AS03 had no effect (FIG. 3b). T-cell polarization was assessed by measuring the release of IFNγ and IL-17, 2 major pathogenic cytokines in EAE, at day 10 in dLN after EAE induction by auto-reactive Tconv cells specific to the $MOG_{35-55}$ immunizing peptide. AS01 administration was associated with a decrease of IFNγ production, whereas IFNγ and IL-17 were unaffected by AS03 administration (FIG. 3c). Thus, although both AS01 and AS03 administration prevented EAE development, only AS01 disrupted priming and polarization of $MOG_{35-55}$ reactive T-cells.

We then performed adoptive transfer experiments to further analyze the role of Treg cells in adjuvant-driven EAE prevention. Purified Treg cells from dLN of adjuvant treated mice were injected into naive mice prior to EAE induction. Amazingly, mice that received Treg cells from AS03 treated mice were fully protected from the disease. In contrast, Treg cells from AS01 treated mice had no effect since recipients mice transferred with these cells developed the same EAE as control mice transferred with PBS or Treg from naive mice (FIG. 3d). These data reveal that AS03 administration strongly enhanced the capacity of Treg cells to control EAE.

To gain more insight into the mechanism of EAE prevention by AS03, we further studied Treg cells and molecules involved in T-cell migration. Cells from dLN of mice immunized to induce EAE and treated with AS03 were analyzed at day 10. Treg cell proportion was significantly increased in AS03 treated mice compare to control (FIG. 3e). The expression of the CCR6 and CXCR3 chemokine receptors by Tconv cells, which play a critical role in the entry of pathogenic T cells into the central nervous system (CNS) during EAE (Reboldi et al. (2009) Nat. Immunol. 10: 514; Sporici and Issekutz (2010) Eur. J. Immunol. 40: 2751), was unaffected by the AS03 treatment (FIG. 4c). Interestingly, the expression levels of integrins involved in CNS homing (Yednock et al. (1992) Nature 356: 63; Rothhammer et al. (2011) J. Exp. Med. 208: 2465) were significantly modified by the adjuvant. Treg cells expressed a higher level of integrin αL while Tconv cells showed a decreased level of integrin αM (FIG. 3f). Moreover, expression levels of integrins α4 and αL by Tconv cells were unaffected (FIG. 4d). These results suggest that AS03 administration impacts on migration of Treg and Tconv cells in the CNS, which may explain its capacity to suppress EAE.

CONCLUSION

This work demonstrates that some of the new generation vaccine adjuvants have strong immuno-regulatory properties and impact on Treg cell activation and function, thus revealing their potential in the treatment of autoimmune disorders. Both AS01 and AS03 administration induced protection from EAE. Interestingly, their suppressive mechanism appears different. AS01 altered priming and cytokine polarization of encephalitogenic Tconv cells whereas AS03 strongly increased the protective capacity of Treg cells in EAE and may modify the migration of Tconv and Treg cells.

The invention claimed is:

1. A method for delaying the onset of and/or treating an autoimmune disease comprising:
   administering an adjuvant to a subject in need thereof, wherein the adjuvant does not comprise aluminium and is suitable for use in a human subject, and wherein the adjuvant is administered in a therapeutically effective amount to enhance immune suppressive capacity of Treg cells,
   with the proviso that the adjuvant does not contain glucopyranosyl lipid adjuvant,
   wherein the autoimmune disease is a disease selected from the group consisting of multiple sclerosis, type 1 diabetes, rheumatoid arthritis, inflammatory bowel diseases, systemic lupus erythematosus, psoriasis, scleroderma, and autoimmune thyroid diseases.

2. The method of claim 1, wherein the adjuvant comprises an immunologically active saponin.

3. The method of claim 2, wherein the adjuvant comprises QS21.

4. The method of claim 2, wherein the adjuvant comprises a sterol.

5. The method of claim 1, wherein the adjuvant comprises a TLR agonist.

6. The method of claim 1, wherein the adjuvant comprises 3-O-deacylated monophosphoryl lipid A.

7. The method of claim 1, wherein the adjuvant comprises QS21 and 3-O-deacylated monophosphoryl lipid A in a liposomal formulation.

8. The method of claim 1, wherein the adjuvant comprises an oil-in-water emulsion.

9. The method of claim 8, wherein the emulsion comprises squalene.

10. The method of claim 9, wherein the emulsion further comprises alpha tocopherol and polyoxyethylene sorbitan monooleate in an aqueous phase.

11. The method of claim 1, wherein the autoimmune disease is multiple sclerosis.

12. The method of claim 1, wherein the autoimmune disease is type 1 diabetes.

13. The method of claim 1, wherein the subject is a human patient.

14. The method of claim 1, wherein the method is a method for delaying the onset of an autoimmune disease in a human patient who is pre-disposed to develop the autoimmune disease.

15. The method of claim 5, wherein the TLR agonist is a TLR4 agonist.

16. The method of claim 1, which is a method for delaying the onset of the autoimmune disease.

17. The method of claim 1, which is a method for treating the autoimmune disease.

18. The method of claim 1, wherein the method is a monotherapy method for delaying the onset of and/or treating an autoimmune disease, wherein the adjuvant is the sole therapeutic agent.

19. A monotherapy method for delaying the onset of and/or treating an autoimmune disease comprising:

administering an adjuvant consisting of QS21, a lipopolysaccharide and cholesterol in a liposomal formulation to a subject in need thereof in a monotherapy method;

wherein the adjuvant is administered in a therapeutically effective amount to enhance immune suppressive capacity of Treg cells; and wherein the autoimmune disease is a disease selected from the group consisting of multiple sclerosis, type 1 diabetes, rheumatoid arthritis, inflammatory bowel diseases, systemic lupus erythematosus, psoriasis, scleroderma, and autoimmune thyroid diseases.

20. A monotherapy method for delaying the onset of and/or treating an autoimmune disease comprising:

administering an adjuvant consisting of an oil-in-water emulsion of squalene, alpha-tocopherol and polyoxyethylene sorbitan monooleate to a subject in need thereof in a monotherapy method;

wherein the adjuvant is administered in a therapeutically effective amount to enhance immune suppressive capacity of Treg cells; and wherein the autoimmune disease is a disease selected from the group consisting of multiple sclerosis, type 1 diabetes, rheumatoid arthritis, inflammatory bowel diseases, systemic lupus erythematosus, psoriasis, scleroderma, and autoimmune thyroid diseases.

21. The method of claim 19, wherein said disease is multiple sclerosis.

22. The method of claim 20, wherein said disease is multiple sclerosis.

23. A monotherapy method for delaying the onset of and/or treating an autoimmune disease comprising:

administering an adjuvant consisting of an oil-in-water emulsion of squalene, polyoxyethylene sorbitan monooleate and polyoxyethylene sorbitan trioleate to a subject in need thereof in a monotherapy method, wherein the adjuvant is administered in a therapeutically effective amount to enhance immune suppressive capacity of Treg cells; and wherein the autoimmune disease is a disease selected from the group consisting of multiple sclerosis, type 1 diabetes, rheumatoid arthritis, inflammatory bowel diseases, systemic lupus erythematosus, psoriasis, scleroderma, and autoimmune thyroid diseases.

24. The method of claim 23, wherein said disease is multiple sclerosis.

25. The method according to claim 19, wherein the lipopolysaccharide is 3-O-deacylated monophosphoryl lipid A.

26. The method according to claim 19, wherein the lipopolysaccharide is monophosphoryl lipid A.

27. A monotherapy method for delaying the onset of and/or treating an autoimmune disease comprising:

administering an adjuvant consisting of an oil-in-water emulsion of squalene in monotherapy to a subject in need thereof;

wherein the adjuvant is administered in a therapeutically effective amount to enhance immune suppressive capacity of Treg cells; and wherein the autoimmune disease is a disease selected from the group consisting of multiple sclerosis, type 1 diabetes, rheumatoid arthritis, inflammatory bowel diseases, systemic lupus erythematosus, psoriasis, scleroderma, and autoimmune thyroid diseases.

28. The method of claim 27, wherein said disease is multiple sclerosis.

* * * * *

UNITED STATES PATENT AND TRADEMARK OFFICE
CERTIFICATE OF CORRECTION

| | | |
|---|---|---|
| PATENT NO. | : 11,311,618 B2 | Page 1 of 1 |
| APPLICATION NO. | : 16/061524 | |
| DATED | : April 26, 2022 | |
| INVENTOR(S) | : Morel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 301 days.

Signed and Sealed this
Tenth Day of June, 2025

Coke Morgan Stewart
*Acting Director of the United States Patent and Trademark Office*